(12) United States Patent
Huang et al.

(10) Patent No.: US 10,271,737 B2
(45) Date of Patent: Apr. 30, 2019

(54) NONINVASIVE ARTERIAL CONDITION DETECTING METHOD, SYSTEM, AND NON-TRANSITORY COMPUTER READABLE STORAGE MEDIUM

(71) Applicant: National Central University, Taoyuan County (TW)

(72) Inventors: Hui-Yang Huang, Taipei (TW); Chung-Wei Lee, Taipei (TW); Chung-Yi Yang, Kaohsiung (TW); Hon-Man Liu, Taipei (TW); Norden Eh Huang, Bethesda, ND (US)

(73) Assignee: National Central University, Taoyuan County (TW)

( * ) Notice: Subject to any disclaimer, the term of this patent is extended or adjusted under 35 U.S.C. 154(b) by 589 days.

(21) Appl. No.: 14/490,660

(22) Filed: Sep. 18, 2014

(65) Prior Publication Data

US 2016/0081561 A1 Mar. 24, 2016

(51) Int. Cl.
*A61B 5/00* (2006.01)
*A61B 5/02* (2006.01)
*A61B 7/04* (2006.01)

(52) U.S. Cl.
CPC .......... *A61B 5/02007* (2013.01); *A61B 7/045* (2013.01); *A61B 5/6898* (2013.01); *A61B 5/7203* (2013.01)

(58) Field of Classification Search
CPC ... A61B 5/02007; A61B 7/045; A61B 5/6898; A61B 5/7203
See application file for complete search history.

(56) References Cited

U.S. PATENT DOCUMENTS

| 4,598,417 A | * | 7/1986 | Deno | A61B 7/04 181/131 |
| 4,768,519 A | * | 9/1988 | Yamaguchi | A61B 7/045 600/493 |
| 5,109,863 A | | 5/1992 | Semmlow et al. | |
| 5,913,826 A | * | 6/1999 | Blank | A61B 5/02007 600/500 |

(Continued)

FOREIGN PATENT DOCUMENTS

CN 101518439 A 9/2009

OTHER PUBLICATIONS

Laurie A. Tomlinson, Methods for assessing arterial stiffness: technical considerations, Lippincott Williams & Wilkins, 2012 Wolters Kluwer Health, vol. 21.

(Continued)

*Primary Examiner* — Tiffany Weston
*Assistant Examiner* — Tho Q Tran
(74) *Attorney, Agent, or Firm* — CKC & Partners Co., LLC (57) ABSTRACT

A noninvasive arterial condition detecting system includes a processing device and an electronic stethoscope configured for auscultating carotid artery to receive sound signals. The processing device is connected to the electronic stethoscope. The processing device records the sound signals, preprocesses the sound signal to reduce noise, measures a trough-peak distance and a trough-peak time, and generates an estimate result of arterial conditions according to the trough-peak distance and the trough-peak time. The trough-peak distance and the trough-peak time are related to the health of the carotid artery walls.

2 Claims, 5 Drawing Sheets

(56) References Cited

U.S. PATENT DOCUMENTS

| | | | |
|---|---|---|---|
| 8,684,943 B2 | 4/2014 | Schmidt et al. | |
| 2001/0050992 A1* | 12/2001 | Carman | A61B 7/04 |
| | | | 381/67 |
| 2003/0229289 A1* | 12/2003 | Mohler | A61B 5/04023 |
| | | | 600/508 |
| 2005/0090755 A1* | 4/2005 | Guion | A61B 7/00 |
| | | | 600/528 |
| 2006/0167385 A1* | 7/2006 | Guion | A61B 7/00 |
| | | | 600/586 |
| 2008/0084538 A1* | 4/2008 | Maeda | A61B 3/1241 |
| | | | 351/206 |
| 2011/0054352 A1* | 3/2011 | Ko | A61B 5/0002 |
| | | | 600/586 |
| 2014/0107515 A1* | 4/2014 | Lee | A61B 7/026 |
| | | | 600/528 |
| 2016/0081561 A1* | 3/2016 | Huang | A61B 5/02007 |
| | | | 600/481 |

OTHER PUBLICATIONS

OMRON Cardio Vascular Profiling System VP-1000/2000, Non-invasive Vascular Screening Device BP-203RPE II, Pulse Wave Unit TU-100 Operation Manual, P.No. 1730486B, Aug. 2006.

Sugawara J, Hayashi K, Yokoi T, et al. "Brachial-ankle pulse wave velocity: an index of central arterial stiffness?", Journal of Human Hypertension (2005) 19, 401-406.

* cited by examiner

NONINVASIVE ARTERIAL CONDITION DETECTING METHOD, SYSTEM, AND NON-TRANSITORY COMPUTER READABLE STORAGE MEDIUM

BACKGROUND

Field of Invention

The present disclosure relates to an arterial condition detecting method, system, and non-transitory computer readable storage medium, and more particularly, a noninvasive arterial condition detecting method, system, and non-transitory computer readable storage medium.

Description of Related Art

A stroke occurs when a blood vessel carrying oxygen and nutrients to the brain bursts or is blocked by a clot, and causes the brain to starve. If deprived of oxygen for even a short period of time, the brain nerve cells start to die. It is the No. 4 cause of death and a leading cause of disability in the United States. It also has serious negative impact on quality of life. Stroke patients suffer from depression and loss of memory in psychological aspect, and encounter difficulties in speech, mobility, and excretion in physical aspect.

Patients with carotid artery diseases, including those with arterial stiffness and a stenosis, have a considerable risk of stroke. Identification of risk factors for cerebrovascular disease in these patients may improve risk profiling and help the prevention of stroke.

Today several non-invasive techniques for measuring/detecting the severity of an arterial condition exist. This can be done by magnetic resonance imaging (MRI), in vivo intravascular ultrasound (IVUS), arteriography, or optical coherence tomography (OCT). However, the above-mentioned techniques are all rather complicated and expensive to use and therefore only patients with specific symptoms are offered such examinations. The consequence is that most patients have a critical arterial condition when examined.

SUMMARY

One aspect of the present disclosure is directed to a noninvasive arterial condition detecting system. The noninvasive arterial condition detecting system includes a processing device and an electronic stethoscope configured for auscultating carotid artery to receive sound signals. The processing device records the sound signals, preprocesses the sound signal to reduce noise, measures a trough-peak distance and a trough-peak time, and generates an estimate result of arterial conditions according to the trough-peak distance and the trough-peak time.

Another aspect of the present disclosure is directed to a noninvasive arterial condition detecting method. The noninvasive arterial condition detecting method includes the following operations: receiving sound signals from an electronic stethoscope placed on a neck for auscultating carotid artery; recording and preprocessing the sound signals to reduce noise; measuring a trough-peak distance and a trough-peak time of the sound signals; and generating an estimate result of arterial conditions according to the trough-peak distance and the trough-peak time.

Yet another aspect of the present disclosure is directed to a non-transitory computer readable storage medium to store a computer program to execute a noninvasive arterial condition detecting method. The noninvasive arterial condition detecting method includes the following operations: receiving sound signals from an electronic stethoscope placed on a neck for auscultating carotid artery; recording and preprocessing the sound signals to reduce noise; measuring a trough-peak distance and a trough-peak time of the sound signals; and generating an estimate result of arterial conditions according to the trough-peak distance and the trough-peak time.

It is to be understood that both the foregoing general description and the following detailed description are by examples, and are intended to provide further explanation of the invention as claimed.

BRIEF DESCRIPTION OF THE DRAWINGS

The present disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
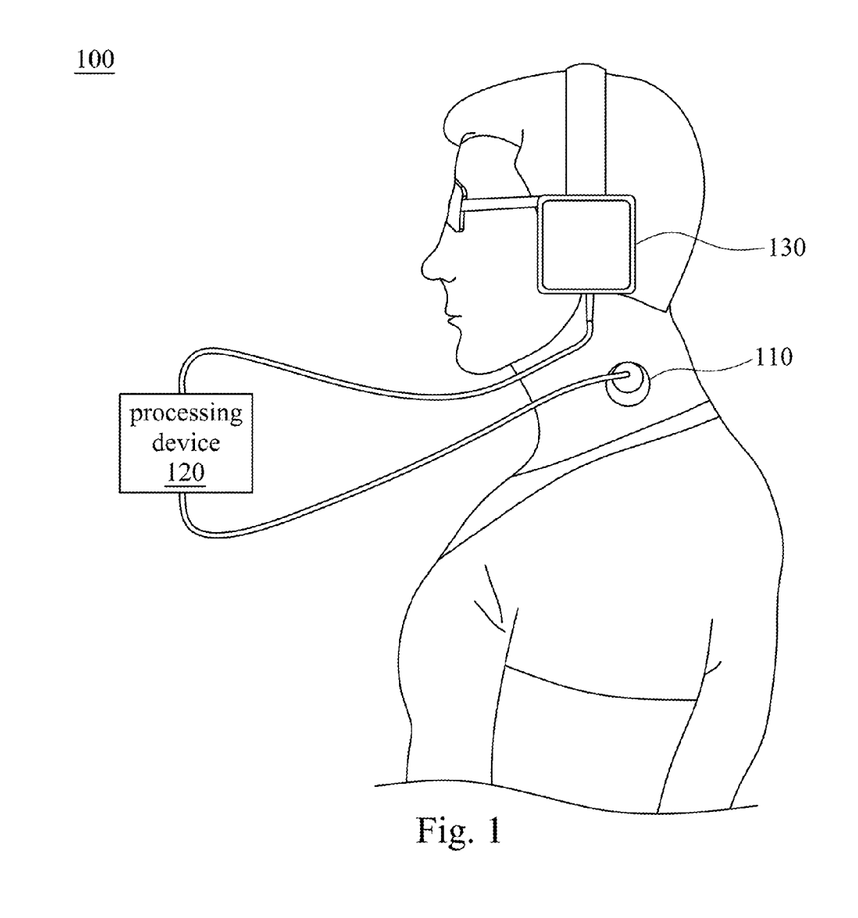
FIG. 1 is a schematic diagram of a noninvasive arterial condition detecting system according to a first embodiment of the present disclosure.

FIG. 1 is a schematic diagram of a noninvasive arterial condition detecting system according to a first embodiment of the present disclosure. The noninvasive arterial condition detecting system 100 includes an electronic stethoscope 110, a processing device 120, and an earphone 130.

The electronic stethoscope 110 converts acoustic sound waves to sound signals in an electronic form. Health conditions of the carotid artery are important risk factors of strokes, because the blood is sent to the brain through carotid arteries. Therefore, the electronic stethoscope 110 is configured to auscultate the blood flow sound of carotid artery to extract useful features to estimate arterial conditions.

In one embodiment, the electronic stethoscope 110 uses a piezoelectric crystal at the head of a metal shaft as a transducer. In another embodiment, the transducer in the electronic stethoscope 110 is an electromagnetic diaphragm with a conductive inner surface to forms a capacitive sensor. In yet another embodiment, the electronic stethoscope is also a wireless device communicating with the processing device via a Bluetooth or WiFi connection.

The processing device 120 is an electronic device connected to the electronic stethoscope 110, and has computing power to process the sound signals received from the electronic stethoscope 110. In one embodiment, the processing device 120 is a personal mobile device such as a smart phone or a tablet. In another embodiment, the processing device 120 is a microcontroller or an application specific integrated circuit (ASIC), customized for the noninvasive arterial condition detecting system 100. In yet another embodiment, the processing device 120 is a personal computer.

The processing device 120 records the sound signals and preprocesses the sound signal to reduce noise. The sound signals are recorded as segments, and the duration of each segment is at least longer than one cardiac cycle for feature extraction. Human heart rate is normally between 60 to 100 beats per minute, which means the duration of the segment is at least between 0.6 to 1 seconds. In one embodiment, the duration of the recorded segments of the sound signals is 1 minute to include multiple cardiac cycles. In another embodiment, the duration of recorded segments of the sound signals is 5 minutes.

The sound signals are preprocessed to reduce noise from the patient sounds and movements, small movements of the electronic stethoscope 110, and environment background noise. In one embodiment, adaptive filtering is used to reduce the noise from the above-described source. In another embodiment, wavelet denoising technique is used for noise reduction.

Figure 2:
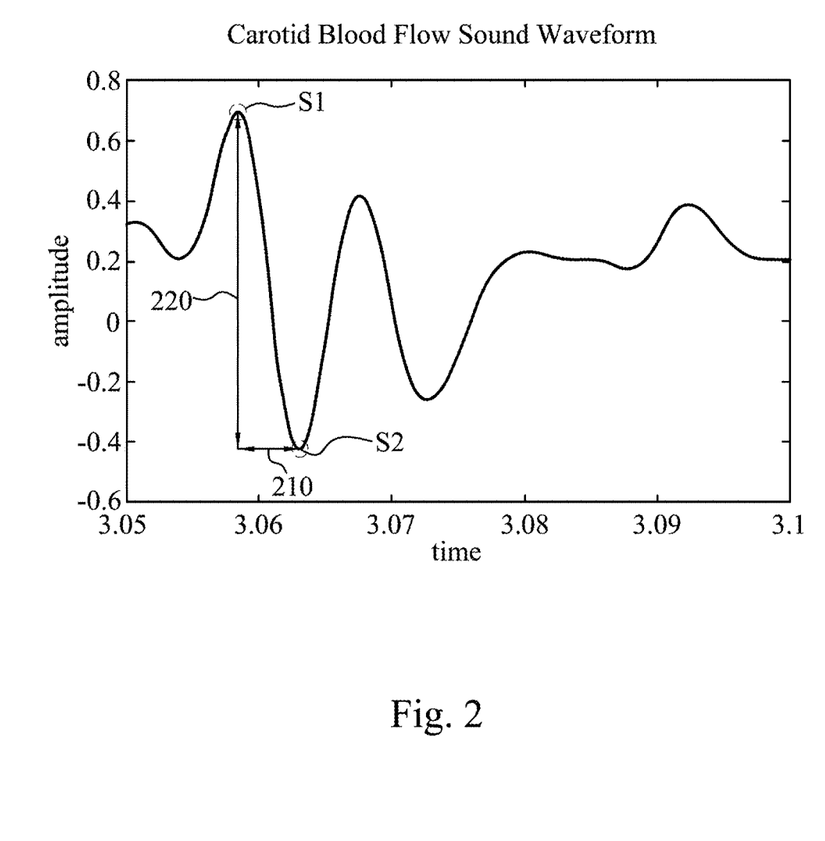
FIG. 2 is a graph of typical carotid blood flow sound waveform.

FIG. 2 is a graph of typical carotid blood flow sound waveform. In FIG. 2, the x-axis represents time, and the y-axis represents amplitude of the sound pressure. The segments of the sound signals recorded by the processing device 120 contain multiple sub-segments similar to the graph shown in FIG. 2. The peak S1 is associated with systole, the part of cardiac cycle in which the heart muscle contracts to force blood into main blood vessels. The force of the blood pumped into the vessels is exerted on elastic walls of carotid arteries, and produces blood flow sound as the mechanism of drums.

Since the walls of the carotid arteries are elastic, they vibrate after hit by the blood pumping force and generate the ripple waveform as shown in FIG. 2. The first valley S2 represents resilience of the carotid arterial walls. Healthy carotid arteries with elastic walls spring back quickly with little amplitude attenuation. In other words, an amplitude difference and a time difference between the first peak S1 and a first valley S2 are related to arterial conditions, and are called a trough-peak distance 220 and a trough-peak time 210, respectively.

As the elasticity of the walls of the carotid arteries decreases or the severity of arterial stenosis increases, the response of the walls of the carotid arteries becomes slower and the amplitude attenuates quickly, which means the trough-peak time 210 increases and the trough-peak distance 220 decreases. In the present disclosure, the trough-peak time 210 and the trough-peak distance 220 are utilized to serve as indicators of arterial conditions and generate an estimate result of arterial conditions.

The arterial conditions are related to various clinical parameters, such as age, gender, and ethnicity, etc. Accordingly, ranges of the trough-peak time 210 and trough-peak distance 220 also vary according to the clinical parameters. In one embodiment, a first threshold value for the trough-peak distance 220 and a second threshold value for the trough-peak time 210 are determined according to the clinical parameters. In other words, nominal values of users of groups associated with different sets of clinical parameters are determined. The more the measured results of the trough-peak time 210 and trough-peak distance 220 deviates from the nominal values in an unfavorable way, the higher the risk of having arterial conditions related to stroke is.

In one embodiment, the first threshold value and the second threshold value are obtained with sample data of the sound signals of carotid arteries collected from subjects of different age groups and genders, such as male 30-40 years old, female 30-40 years old, male 40-50 years old, female 40-50 years old, male 50-60 years old, female 50-60 years old, male more than 60 years old, and female more than 60 years old. Each group includes at least 10 subjects, and the sample data of each subject includes 5 2-minute segments of the sound signals recorded from carotid arteries auscultation. The first threshold value and the second threshold value are the averages of the trough-peak distance 220 and trough-peak time 210 measured in the 50 segments (5 segments for 10 subjects). The division of age groups and the number of segments of each subject described herein are only for example and should not be used to limit the present disclosure.

In another embodiment, the first threshold value and the second threshold value are the upper quartile value of all trough-peak distance 220 and trough-peak time 210 from the sample data, respectively. In yet another embodiment, the subjects of the training data are further divided into a smoking group and non-smoking group.

The trough-peak distance 220 and the trough-peak time 210 measured from user are respectively compared to the first threshold value and the second threshold value obtained from the above-described training data to generate the estimate result of arterial conditions. When the trough-peak distance 220 is smaller than the first threshold value or the trough-peak time 210 is larger than the second threshold value, the arterial condition is estimated to be abnormal, and the user is advised to consult a doctor.

These two indicators are easy to measure noninvasively, thus avoiding the expensive cost of examination and brings convenience for people with high stroke risk to monitor their own health regularly at home. Moreover, the noninvasive arterial condition detecting system 100 can be implemented on a personal mobile device, which further facilitates detecting signs of arterial conditions early and take preventive measures before stroke happens.

The noninvasive arterial condition detecting system 100 also includes the earphone 130. The earphone 130 is connected to the processing device 120 to receive the sound signal from the electronic stethoscope 110 in real-time for aiding to position the electronic stethoscope 110 for auscultating the carotid artery. With aid from the earphone 130, users without formal medical training can easily locate the carotid arteries by listening whether a clear pulsing sound is present. In one embodiment, the earphone 130 is a pair of in-ear headphones. In another embodiment, the earphone 130 is a pair of noise-canceling headphones to block out the background noise.

Figure 3:
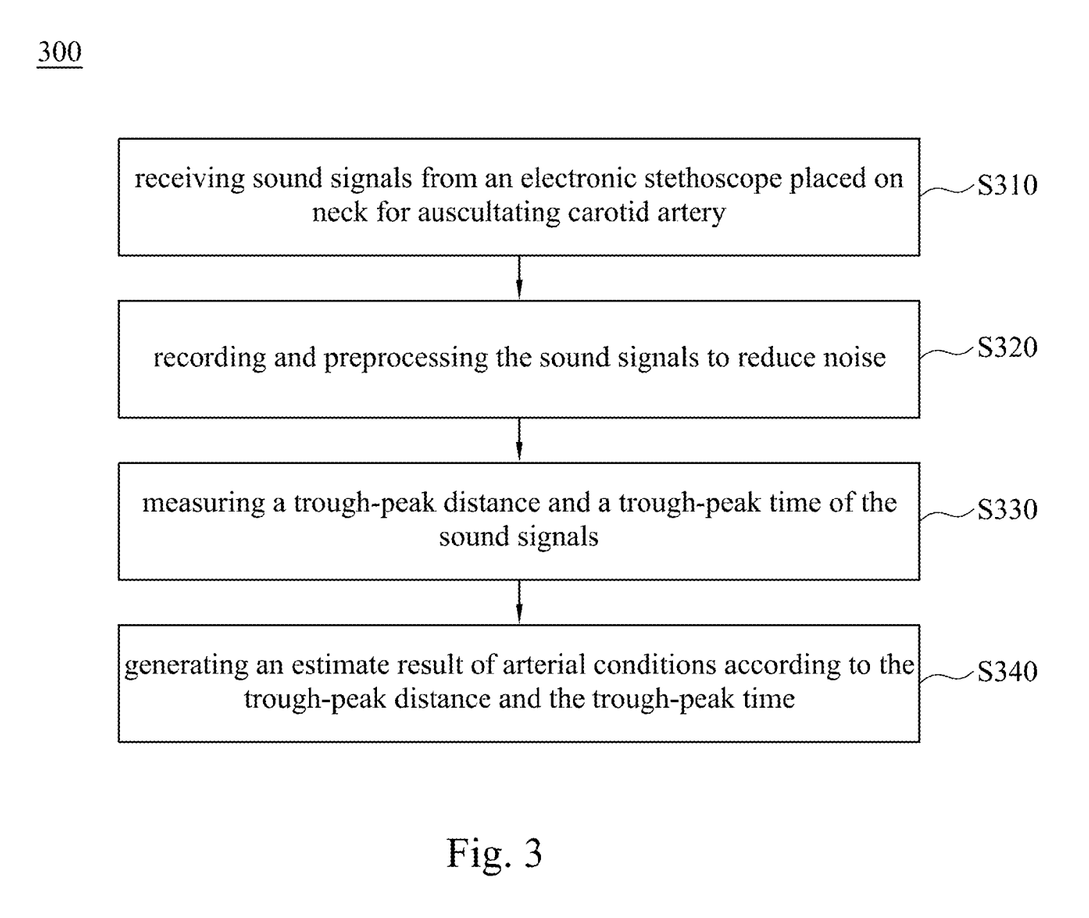
FIG. 3 is a flow chart of a noninvasive arterial condition detecting method according to a second embodiment of the present disclosure.

FIG. 3 is a flow chart of a noninvasive arterial condition detecting method according to a second embodiment of the present disclosure. The noninvasive arterial condition detecting method 300 includes the following operations. For convenience and clarity of explanation, the following explanation of the operations of the noninvasive arterial condition detecting method 300 takes the noninvasive arterial condition detecting system 100 shown in FIG. 1 as an example, but the disclosure is not limited thereto.

Operation S310 is receiving sound signals from an electronic stethoscope 110 placed on a neck for auscultating carotid artery. In one embodiment, an earphone 130 is utilized to aid placing the electronic stethoscope 110 at the correct position to improve the qualities of the sound signals received.

Operation S320 is recording and preprocessing the sound signals to reduce noise. In one embodiment, the sound signals received from the electronic stethoscope 110 are recorded and preprocessed by the processing device 120. The processing device 120 reduce the noise of the sound signals by various techniques such as wavelet denoising, and cut a 2-minute segment from the sound signals recorded and preprocessed according to the signal noise ratio (SNR) for the next operation. In another embodiment, the processing device 120 is combined with the electronic stethoscope 110 by embedding a microcontroller in the electronic stethoscope 110.

Operation S330 is measuring a trough-peak distance 220 and a trough-peak time 210 of the sound signals. The details of this operation is given in the above paragraphs, and therefore not repeated herein. In one embodiment, the recorded and preprocessed segments of the sound signals are of 2 minutes duration, and include 120-200 cardiac cycles. The trough-peak distance 220 and the trough-peak time 210 of each cardiac cycle is measured for the next operation.

Operation S340 is generating an estimate result of arterial conditions according to the trough-peak distance 220 and the trough-peak time 210. In one embodiment, a first threshold value for the trough-peak distance 220 and a second threshold value for the trough-peak time 210 are determined according to clinical parameters. Details of how to determine the first threshold value and the second threshold value are given in the above paragraphs. It is worth noting that the estimate result is generated by comparing the average of the trough-peak distance 220 and the trough-peak time 210 when multiple trough-peak time 210 and trough-peak distance 220 are measured for the segments of the sound signals lasting longer than one cardiac cycle. When the average of the trough-peak distance 220 is smaller than the first threshold value and the average of the trough-peak time 210 is larger than the second threshold value, the estimate result is abnormality and medical consultation is advised.

Figure 4A:
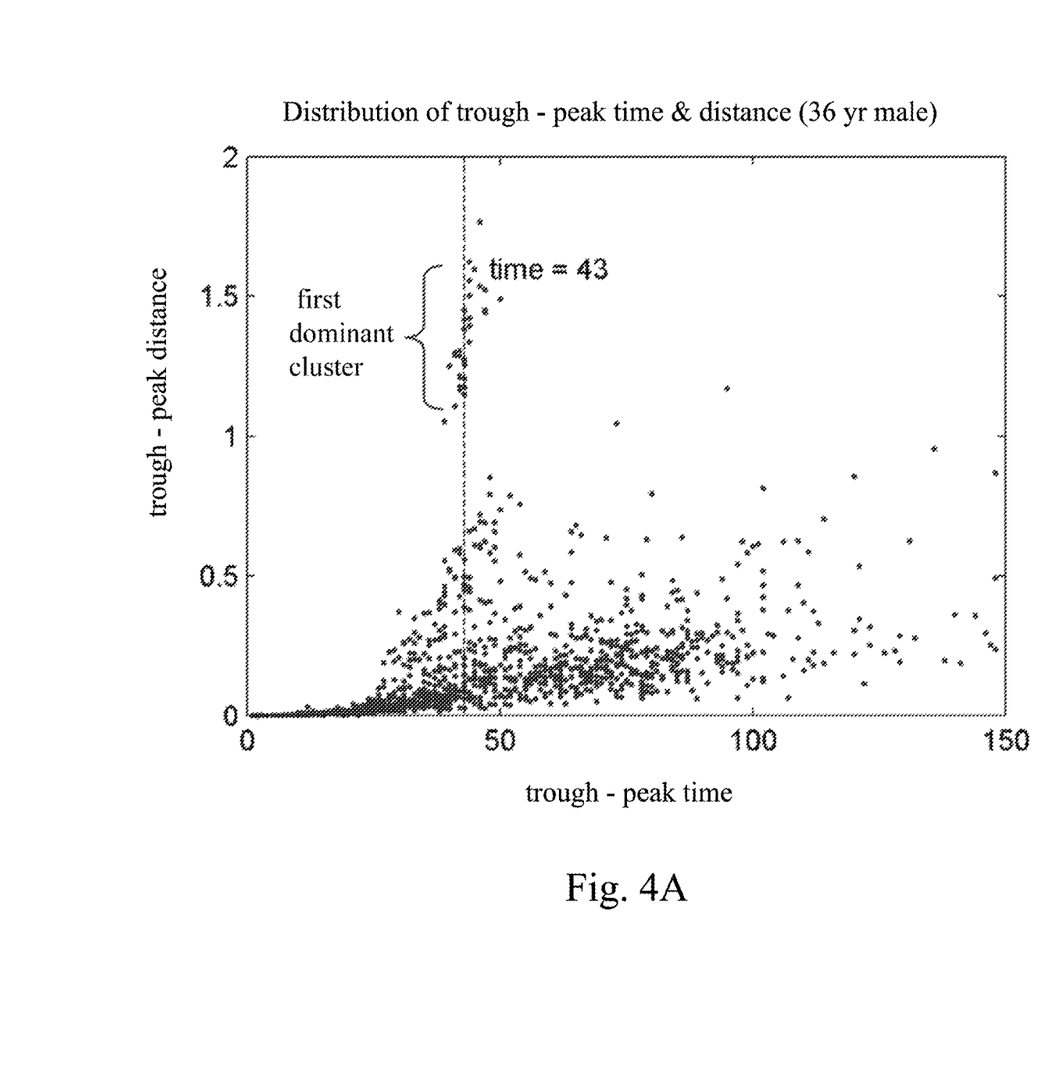
FIG. 4A is a scatter diagram of trough-peak time and trough-peak distance of a first set of clinical parameters.
Figure 4B:
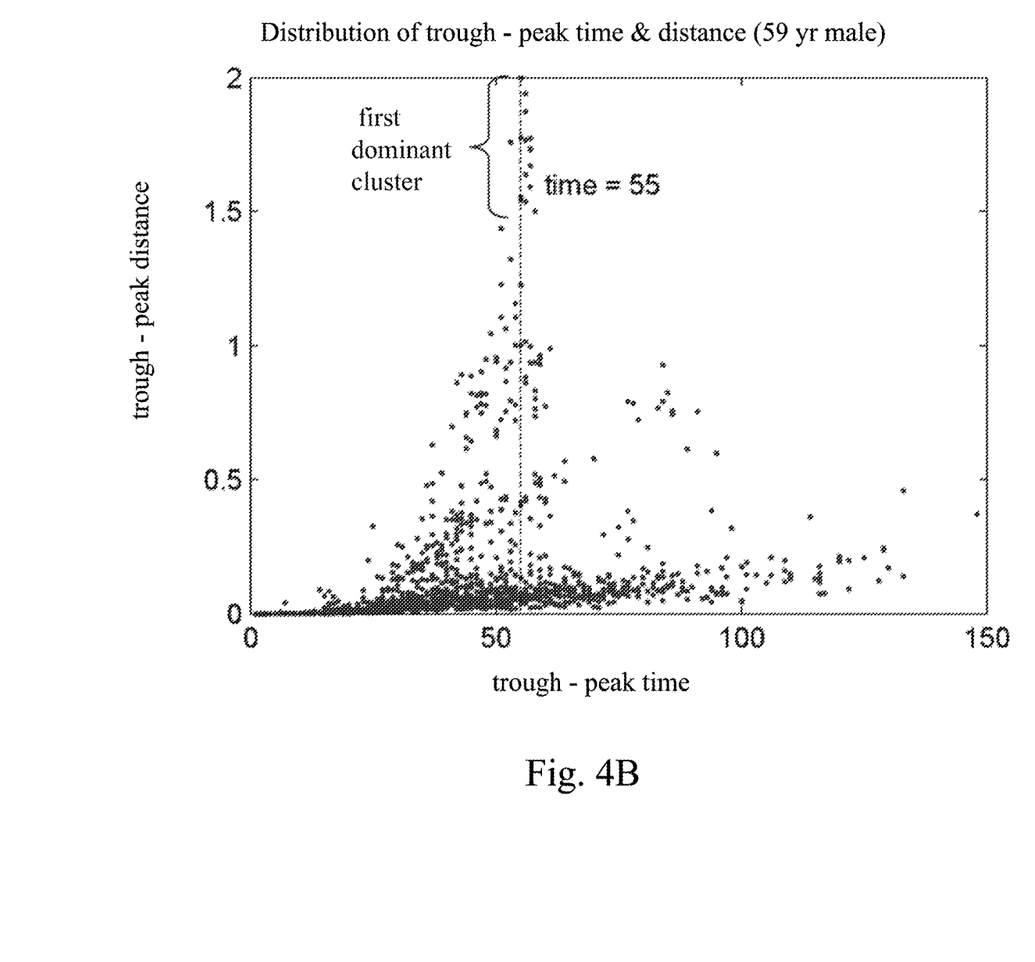
FIG. 4B is a scatter diagram of trough-peak time and trough-peak distance of a second set of clinical parameters

In another embodiment, training data of the sound signals of blood flow sound of carotid arteries collected from subjects associated with different sets of clinical parameters are utilized for machine learning. FIG. 4A and FIG. 4B are scatter diagrams of trough-peak time 210 and trough-peak distance 220 of a first set of clinical parameters (male, 30-40 years old) and a second set of clinical parameters (male, 50-60 years old), respectively. The data points falling into the bracketed parts are trough-peak time 210 and trough-peak distance 220, which are the time difference and amplitude difference between the first peak S1 and the first valley S2 associated with systole of each cardiac cycle.

The scatter diagrams of the segments of the sound signals obtained from subjects with or without arterial conditions are divided into groups associated with different sets of clinical parameters, and utilized as training data of machine learning algorithm (e.g. Support Vector Machine, Relevance Vector Machine or Bayesian Networks) to find the patterns of the scatter diagrams of the trough-peak time 210 and trough-peak distance 220. The patterns acquired from the training stage are pre-loaded in the processing device 120. The noninvasive arterial condition detecting method 300 or the noninvasive arterial condition detecting system 100 matches the scatter diagram of the trough-peak distance 220 and trough-peak time 210 to the patterns associated with the same clinical parameters as the user, and generate the estimate result according to the matching result.

In yet another embodiment, the processing device 120 further includes a display (not shown in the figure) to display the scatter diagram generated from the sound signals received from the user together with the scatter diagram of a subject with healthy carotid arteries with the same clinical parameters as the user to visualize the estimate result.

The trough-peak time 210 and the trough-peak distance 220 are features extracted from the sound signals of carotid artery auscultation, and there are other features contained in the sound signals, which are useful for detecting the arterial conditions. For example, the Gammatone filterbank generates an envelope feature of the sound signal, and the shape of the envelope is also related to the elasticity of the walls of the carotid arteries. Longer envelope indicates slower attenuation and better elasticity, Moreover, the Hilbert-Huang Transform generates frequency data associated with the sound signals, and can be used as features to detect arterial conditions as well. The above-mentioned features are integrable with the trough-peak distance 220 and the trough-peak time 210 to generate the estimate result.

The noninvasive arterial condition detecting method 300 may take the form of a computer program product stored on a computer-readable storage medium having computer-readable instructions embodied in the medium. The operation of the computer program is described in details in the above paragraphs, and therefore not repeated herein. Any suitable storage medium may be used including non-volatile memory such as read only memory (ROM), programmable read only memory (PROM), erasable programmable read only memory (EPROM), and electrically erasable programmable read only memory (EEPROM) devices; volatile memory such as static random access memory (SRAM), dynamic random access memory (DRAM), and double data rate random access memory (DDR-RAM); optical storage devices such as compact disc read only memories (CD-ROMs) and digital versatile disc read only memories (DVD-ROMs); and magnetic storage devices such as hard disk drives (HDD) and floppy disk drives.

The noninvasive arterial condition detecting system 100 and the noninvasive arterial condition detecting method 300 offer various advantages. The usage does not take professional medical knowledge. Moreover, they are cost-effective such that people with high stroke risk can monitor their own health at home regularly before the arterial conditions become severe.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A noninvasive arterial condition detecting system, comprising:
    an electronic stethoscope configured for auscultating a carotid artery to receive a sound signal;
    a processing device connected to the electronic stethoscope; and
    an earphone connected to the processing device to receive the sound signal from the electronic stethoscope in real-time for aiding to position the electronic stethoscope for auscultating the carotid artery,
    wherein the processing device is configured to record the sound signal, to preprocess the sound signal to reduce noise, to identify sound wave peaks consecutively from the sound signal and valleys adjacent to the sound wave peaks consecutively from the sound signal, to calculate a trough-peak amplitude distance and a trough-peak time distance between every peak and every left-sided valley adjacent to said every peak, to calculate a trough-peak amplitude distance and a trough-peak time distance between said every peak and every right-sided valley adjacent to said every peak, and to generate an estimate result of an arterial condition according to a distribution of both of the trough-peak amplitude distance and the trough-peak time distance, the distribution is generated using a 2-D (two-dimensional) graph, wherein the arterial condition comprises parameters related to an elasticity of arterial walls or a formation of arterial stenosis, wherein the processing device is configured to identify a first dominant cluster from the distribution with a highest mean value of trough-peak amplitude distance in the 2-D graph of trough-peak amplitude distance and trough-peak time distance, to estimate the mean value of trough-peak amplitude distance of the first dominant cluster, to compare the mean value of trough-peak amplitude distance of the first dominant cluster with a first threshold value, and when the mean trough-peak amplitude distance of the first dominant cluster is smaller than the first threshold value, the processing device is configured to determine that the estimate result is abnormality of the arterial condition, wherein the first threshold value is an average of trough-peak amplitude distances of different age groups and genders of sample data, wherein the processing device comprises a display to show the estimate result.

2. The noninvasive arterial condition detecting system as claimed in claim 1, wherein the processing device is configured to estimate a mean value of trough-peak time distance of the first dominant cluster, to compare the mean value of trough-peak time distance of the first dominant cluster with a second threshold value, and when the trough-peak time distance is larger than the second threshold value, the processing device is configured to determine that the estimate result is abnormality of the arterial condition, wherein the second threshold value is an average of trough-peak time distances within an age group and genders of sample data.

* * * * *